United States Patent [19]
Mitani et al.

[11] Patent Number: 5,973,216
[45] Date of Patent: Oct. 26, 1999

[54] METHOD FOR PRODUCING BROMOMETHYLCYCLOPROPANE

[75] Inventors: Toshimichi Mitani, Kurashiki; Tatsuhiko Hayashibara, Kitakanbara-gun; Manzo Shiono, Kurashiki, all of Japan

[73] Assignee: Kuraray Co., Ltd., Kurashiki, Japan

[21] Appl. No.: 09/023,079

[22] Filed: Feb. 13, 1998

[30] Foreign Application Priority Data

Feb. 13, 1997 [JP] Japan .................................. 9-029085

[51] Int. Cl.$^6$ ............................ C07C 17/16; C07C 19/00
[52] U.S. Cl. ............................................ 570/261; 570/241
[58] Field of Search ..................................... 570/241, 261

[56] References Cited

FOREIGN PATENT DOCUMENTS 0 565 826  10/1993  European Pat. Off. .
WO 97/30958  8/1997  WIPO .

OTHER PUBLICATIONS

Roberts, et al, *Interconversion of Cyclobutyl and Allylcarbinyl Derivatives*, vol. 73, pp. 2509–2520 (1951).

Hrubiec, et al, *J. Org. Chem.*, vol. 49, pp. 431–435 (1984).

*Primary Examiner*—Alan Siegel
*Attorney, Agent, or Firm*—Oblon, Spivak, McClelland, Maier & Neustadt, P.C.

[57] ABSTRACT

A method for producing bromomethylcyclopropane is provided, comprising reacting an organic sulfonyl halide with cyclopropylmethanol in the presence of a tertiary amine in a non-protic solvent, to generate cyclopropylmethyl organic sulfonate, and reacting the resulting cyclopropylmethyl organic sulfonate with an alkali metal bromide and/or a quaternary ammonium bromide in a non-protic polar solvent.

13 Claims, No Drawings

METHOD FOR PRODUCING BROMOMETHYLCYCLOPROPANE

BACKGROUND OF THE INVENTION

1. Field of the Invention

The present invention relates to a method for producing bromomethylcyclopropane having a high purity. The bromomethylcyclopropane of the present invention is useful as a raw material of pharmaceutical products.

2. Discussion of the Related Art

Conventional methods for producing bromomethylcyclopropane, for example, include a method comprising reacting methanesulfonyl bromide with cyclopropylmethanol in the presence of a tertiary amine under heating (EP 565826), a method comprising reacting a dimethylsulfide-bromine complex with cyclopropylmethanol (Chem. Commun., p.212 (1973)), and a method comprising reacting phosphorus tribromide with cyclopropylmethanol (J. Am. Chem. Soc., p.2509 (1951)); however, in these methods, the ring-opening reaction of the cyclopropane ring or the isomerization thereof into bromocyclobutane is progressed, so that bromomethylcyclopropane with a high purity, as required for pharmaceutical usages, cannot be obtained.

A method for producing bromomethylcyclopropane at a high purity, suitable for pharmaceutical use, is known comprising brominating cyclopropylmethanol with triphenylphosphine-dibromide (J. Org. Chem., Vol.49, p.431 (1984) and WO 97/30958). However, this method is not appropriate for industrial practice, because it presents the disadvantages of having to use triphenylphosphine dibromide which is expensive and because the process generates large amounts of phosphorus waste.

Therefore, there is a need for an industrially advantageous method to produce bromomethylcyclopropane with a high purity, and at relatively low cost.

SUMMARY OF THE INVENTION

Accordingly, it is an object of the present invention to provide a method for the production of bromomethylcyclopropane at a high purity, by using a highly stereoselective reaction which is suitable for industrial production.

More specifically, in an embodiment of the present invention, it is provided a method for producing halogenomethylcyclopropane, comprising reacting an organic sulfonyl halide with cyclopropylmethanol in the presence of a tertiary amine in a non-protic solvent, to generate cyclopropylmethyl organic sulfonate, and reacting the resulting cyclopropylmethyl organic sulfonate with an alkali metal bromide and/or a quaternary ammonium bromide in a non-protic polar solvent.

DETAILED DESCRIPTION OF THE INVENTION

The non-protic solvent includes, but is not limited to, a polar solvent such as dimethylformamide, dimethylacetamide, dimethylimidazolidinedione, N-methylpyrrolidone, dimethylsulfoxide and sulfolane; and a halogenated hydrocarbon such as methylene chloride and dichloroethane. Among them, preference is given to dimethylformamide, dimethylimidazolidinedione, and N-methylpyrrolidone. The amount of the non-protic solvent to be used is preferably, but is not limited to, an amount within a range of 0.1 to 100 parts by weight based on the weight of cyclopropylmethanol, provided that the solvent at the specified amount can be agitated.

The tertiary amine includes for example a trialkylamine such as trimethylamine, triethylamine, trioctylamine, and diisopropylethylamine; an aromatic amine such as dimethylaniline and diethylaniline; and a nitrogen-containing heterocyclic compound such as N-methylmorpholine, pyridine, picoline, lutidine, and quinoline. The amount of the tertiary amine to be used is preferably within a range of 0.8 to 5 molar equivalents based on the amount of the organic sulfonyl halide.

The organic sulfonyl halide includes for example an alkanesulfonyl halide, and an arenesulfonyl halide. The alkanesulfonyl halide includes for example an alkanesulfonyl chloride such as methanesulfonyl chloride and ethanesulfonyl chloride; and an alkanesulfonyl bromide such as methanesulfonyl bromide; arenesulfonyl halide includes for example an arenesulfonyl chloride such as benzenesulfonyl chloride, toluenesulfonyl chloride, and p-chlorobenzenesulfonyl chloride; an arenesulfonyl bromide such as benzenesulfonyl bromide. The amount of the organic sulfonyl halide to be used is preferably within a range of 0.8 to 1.2 molar equivalents based on cyclopropylmethanol.

The non-protic polar solvent to be used for the reaction of cyclopropylmethyl organic sulfonate with alkali metal bromide and/or quaternary ammonium bromide includes, for example, dimethylformamide, dimethylacetamide, dimethylimidazolidinedione, N-methylpyrrolidone, dimethylsulfoxide, and sulfolane. Among them, preference is given to dimethylformamide, dimethylimidazolidinedione, and N-methylpyrrolidone. The amount of the non-protic polar solvent to be used is appropriately within the range of the amount to be able to stir the reaction mixture. When the non-protic polar solvent is used for the reaction of cyclopropylmethanol with the organic sulfonyl halide, the reaction of cyclopropylmethyl organic sulfonate with the alkali metal bromide and/or the quaternary ammonium bromide can continuously be effected in the non-protic polar solvent. When non-protic solvents, excluding non-protic polar solvents, are used for the reaction of cyclopropylmethanol with organic sulfonyl halide, the solvent is substituted with non-protic polar solvent in the reaction of cyclopropylmethyl organic sulfonate with an alkali metal bromide and/or quaternary ammonium bromide.

The alkali metal bromide includes for example sodium bromide, potassium bromide, lithium bromide, and cesium bromide; the quaternary ammonium bromide includes, for example, benzyltrimethylammonium bromide, cetyltrimethylammonium bromide, tetrabutylammonium bromide and tetramethylammonium bromide. The amounts of the alkali metal bromide and/or quaternary ammonium bromide to be used are preferably within a range of 1 to 5 molar equivalents based on the organic sulfonyl halide.

The alkali metal bromide and/or quaternary ammonium bromide may be present in the reaction system, prior to the addition of the organic sulfonyl halide, or may be added to the reaction system after the addition of the organic sulfonyl halide. Additionally, cyclopropylmethanol may be reacted with the organic sulfonyl halide in the presence of a tertiary amine in a non-protic solvent, to generate the resulting hydrogen halide salt of tertiary amine, which is then removed by filtration, followed by addition of the alkali metal bromide and/or quaternary ammonium bromide.

The reaction temperature is preferably within a range of −20° C. to 40° C., more preferably within a range of 0° C. to 30° C., because of ring opening of the cyclopropane ring at a higher temperature.

After termination of the reaction, the isolation and purification of the product from the reaction mixture is carried out by adding a solvent that can phase-separate from the non-protic polar solvent. Examples of solvents that can phase-separate from the non-protic polar solvents include, for example, a hydrocarbon such as hexane, pentane, and cyclohexane, together with water, to the reaction system, to extract the product, rinsing the extract solution with water, aqueous sodium hydrogen carbonate and the like, and evaporating the solvents.

Having generally described this invention, a further understanding can be obtained by reference to certain specific examples which are provided herein for purposes of illustration only and are not intended to be limiting unless otherwise specified.

EXAMPLES

Example 1 cyclopropylmethanol (7.2 g), 1,3-dimethylimidazolidin-2-one (DMI) (25 ml) and triethylamine (12.1 g) were mixed together in nitrogen atmosphere, and the resulting mixture was cooled to −10° C., followed by dropwise addition of methanesulfonyl chloride (11.46 g) over about 50 minutes, while retaining the inner temperature at 0° C. After the addition, the resulting solution was agitated at 0° C. for 30 minutes. Subsequently the resulting crystals were filtered and rinsed with 20 ml of DMI. After combining the filtrate and the rinsing solution together, sodium bromide (30.9 g) was added to the mixture under agitation. Then, the mixture was agitated at room temperature for an additional 4 hours. The resulting reaction solution was cooled in ice, followed by addition of hexane (100 ml) and water (100 ml) while retaining the mixture at 0° C., prior to liquid separation. The organic layer was analyzed. The purity and yield of bromomethylcyclopropane were 99.3% and 84%, respectively. After distilling off hexane from the organic layer, bromomethylcyclopropane was recovered (10.13 g; purity of 99.3% and yield of 75%) by evaporation at reduced pressure. Additionally, the DMI used as the solvent was recovered by extraction with dichloromethane from the aqueous layer.

Example 2

The same reaction and post-treatment were carried out in the same manner as in Example 1, except for the use of N,N'-dimethylformamide instead of the DMI used in Example 1, to recover 10.6 g of bromomethylcyclopropane (purity of 99.4 and yield of 80%).

Obviously, numerous modifications and variations of the present invention are possible in light of the above teachings. It is therefore to be understood that within the scope of the appended claims, the invention may be practiced otherwise than as specifically described herein.

The Priority Document, Japanese Application No. 29085/1997, filed Feb. 13, 1997 is incorporated herewith by reference in its entirety.

We claim:

1. A method for producing bromomethylcyclopropane, comprising reacting an organic sulfonyl halide with cyclopropylmethanol in the presence of a tertiary amine in a non-protic solvent, to generate cyclopropylmethyl organic sulfonate, and reacting the resulting cyclopropylmethyl organic sulfonate with a compound selected from the group consisting of an alkali metal bromide, a quaternary ammonium bromide and a mixture thereof, in a non-protic polar solvent.

2. The method according to claim 1, wherein the reaction is carried out at a temperature in the range of from −20° C. to 40° C.

3. The method according to claim 1, wherein said non-protic solvent is selected from the group consisting of dimethylformamide, dimethylimidazolidinedione and N-methylpyrrolidone.

4. The method according to claim 1, wherein said tertiary amine is selected from the group consisting of a trialkylamine, an aromatic amine and a nitrogen-containing heterocyclic compound.

5. The method according to claim 1, wherein the amount of the tertiary amine to be used is within the range of 0.8 to 5 molar equivalents based on the amount of the organic sulfonyl halide.

6. The method according to claim 1, wherein said organic sulfonyl halide is selected from the group consisting of an alkane sulfonyl halide and an arenesulfonyl halide.

7. The method according to claim 1, wherein said non-protic polar solvent is selected from the group consisting of dimethylformamide, dimethylacetamide, dimethylimidazolidinedione, N-methylpyrrolidone, dimethylsulfoxide and sulfolane.

8. The method according to claim 1, wherein said non-protic polar solvent is selected from the group consisting of dimethylformamide, dimethylimidazolidinedione and N-methylpyrrolidone.

9. The method according to claim 1, wherein the amount of said organic sulfonyl halide is within the range of 0.8 to 1.2 molar equivalents based on cyclopropylmethanol.

10. The method according to claim 1, wherein said alkali metal bromide is selected from the group consisting of sodium bromide, potassium bromide, lithium bromide and cesium bromide; and wherein said quaternary ammonium bromide is selected from the group consisting of benzyltrimethylammonium bromide, cetyltrimethylammonium bromide, tetrabutylammonium bromide and tetramethylammonium bromide.

11. The method according to claim 1, wherein the amount of said alkali metal bromide or quaternary ammonium bromide is in the range of 1 to 5 molar equivalents based on the organic sulfonyl halide.

12. The method according to claim 4, wherein said trialkylamine is selected from the group consisting of trimethylamine, triethylamine, trioctylamine and diisopropylethylamine; wherein said aromatic amine is selected from the group consisting of dimethylaniline and diethylaniline; and wherein said nitrogen-containing heterocyclic compound is selected from the group consisting of N-methylmorpholine, pyridine, picoline, lutidine and quinoline.

13. The method according to claim 6, wherein said alkanesulfonyl halide is selected from the group consisting of methanesulfonyl chloride, ethane sulfonyl chloride and methanesulfonyl bromide; and wherein said arenesulfonyl halide is selected from the group consisting of benzenesulfonyl chloride, toluenesulfonyl chloride, p-chlorobenzenesulfonyl chloride and benzenesulfonyl bromide.

* * * * *